United States Patent
Colburn (10) Patent No.: US 8,905,029 B2
(45) Date of Patent: Dec. 9, 2014

(54) AIRWAY SYSTEM WITH CARBON DIOXIDE SENSOR FOR DETERMINING TRACHEAL CUFF INFLATION AND TECHNIQUE FOR USING THE SAME

(75) Inventor: Joel Colburn, Walnut Creek, CA (US)

(73) Assignee: Covidien LP, Mansfield, MA (US)

( * ) Notice: Subject to any disclaimer, the term of this patent is extended or adjusted under 35 U.S.C. 154(b) by 1115 days.

(21) Appl. No.: 12/552,090

(22) Filed: Sep. 1, 2009

(65) Prior Publication Data

US 2010/0078030 A1    Apr. 1, 2010

Related U.S. Application Data

(60) Provisional application No. 61/101,063, filed on Sep. 29, 2008.

(51) Int. Cl.
*A61M 16/04* (2006.01)
*A61M 16/00* (2006.01)
*A62B 9/06* (2006.01)

(52) U.S. Cl.
CPC ....... *A61M 16/04* (2013.01); *A61M 2016/0413* (2013.01); *A61M 16/044* (2013.01)
USPC .................................................. 128/207.14

(58) Field of Classification Search
USPC ........... 128/207.15, 207.14, 204.23; 600/424, 600/323, 18, 301, 529–543; 604/118, 914, 604/907, 912, 920, 99.01, 100.1–100.3
See application file for complete search history.

(56) References Cited

U.S. PATENT DOCUMENTS

| | | | |
|---|---|---|---|
| 3,720,199 A | * | 3/1973 | Rishton et al. .................. 600/18 |
| 3,931,822 A | | 1/1976 | Marici |
| 4,285,340 A | * | 8/1981 | Gezari et al. ............. 128/205.24 |
| 4,526,196 A | | 7/1985 | Pistillo |
| 4,552,558 A | | 11/1985 | Muto |
| 4,565,194 A | | 1/1986 | Weerda et al. |
| 4,617,015 A | | 10/1986 | Foltz |
| 4,630,606 A | | 12/1986 | Weerda et al. |
| 4,898,168 A | | 2/1990 | Yule |
| 5,218,970 A | | 6/1993 | Turnbull et al. |

(Continued)

FOREIGN PATENT DOCUMENTS

| | | |
|---|---|---|
| WO | 9422518 | 10/1994 |
| WO | 02076279 | 10/2002 |

OTHER PUBLICATIONS

Lomholt, N., A Device for Measuring the Lateral Wall Cuff Pressure of Endotracheal Tubes, Acta Anaesthesiologica Scandinavica, Dec. 1992, pp. 775-778, Issue 36.

(Continued)

*Primary Examiner* — Tan-Uyen T. Ho
*Assistant Examiner* — Mark Wardas
(74) *Attorney, Agent, or Firm* — Fletcher Yoder PC (57) ABSTRACT

An airway management device is provided that may adjust the inflation level of a cuff associated with an endotracheal tube. The cuff inflation may be adjusted in response to an increase in carbon dioxide levels above the cuff, which may indicate a poor seal of the cuff against the tracheal walls, as well in response to a measured intracuff pressure. By using information about the seal quality of the cuff together with information about the cuff pressure, the inflation of the cuff can be adjusted to minimize cuff inflation pressure while maintaining a high quality tracheal seal.

17 Claims, 2 Drawing Sheets

(56) References Cited

U.S. PATENT DOCUMENTS

| | | | |
|---|---|---|---|
| 5,235,973 A | | 8/1993 | Levinson |
| 5,361,753 A | | 11/1994 | Pothmann et al. |
| 5,487,383 A | | 1/1996 | Levinson |
| 5,487,731 A | | 1/1996 | Denton |
| 5,546,935 A | | 8/1996 | Champeau |
| 5,591,130 A | | 1/1997 | Denton |
| 5,740,796 A | | 4/1998 | Skog |
| 5,752,921 A | | 5/1998 | Orr |
| 5,819,723 A | * | 10/1998 | Joseph ............ 128/207.14 |
| 5,885,248 A | | 3/1999 | Denton |
| 5,906,204 A | | 5/1999 | Beran et al. |
| 6,315,739 B1 | | 11/2001 | Merilainen et al. |
| 6,530,898 B1 | | 3/2003 | Nimkar et al. |
| 6,647,984 B1 | * | 11/2003 | O'Dea ............ 128/207.16 |
| 6,651,666 B1 | * | 11/2003 | Owens ............ 128/207.16 |
| 6,820,618 B2 | | 11/2004 | Banner et al. |
| 7,273,050 B2 | | 9/2007 | Wei |
| 2004/0123867 A1 | | 7/2004 | Efrati |
| 2005/0279360 A1 | | 12/2005 | Wei |
| 2007/0062540 A1 | * | 3/2007 | Murray-Harris ......... 128/207.29 |
| 2007/0208252 A1 | * | 9/2007 | Makower ............ 600/424 |
| 2008/0072913 A1 | * | 3/2008 | Baker et al. ............ 128/207.15 |
| 2008/0078394 A1 | | 4/2008 | Ostrowski et al. |
| 2008/0210235 A1 | | 9/2008 | Field et al. |
| 2009/0038620 A1 | | 2/2009 | Efrati |
| 2009/0229605 A1 | * | 9/2009 | Efrati et al. ............ 128/203.12 |

OTHER PUBLICATIONS

Pollard, Richard. J. MD et al., Endotracheal Tube Location Verified Reliably by Cuff Palpation, Anesthesia and Analgesia, 1995, pp. 135-138.

Cardoso, Monica M. S. C. MD et al., Portable Devices Used to Detect Endotracheal Intubation During Emergency Situations: A Review, Critical Care Medicine, May 1998, pp. 957-964, vol. 26, Issue 5.

Guttmann, Josef PhD et al., Continuous Calculation of Intratracheal Pressure in the Presence of Pediatric Endotracheal Tubes, Critical Care Medicine, Apr. 2000, pp. 1-21, vol. 28, Issue 4.

Karasawa, Fujio. MD et al., Profile Soft-Seal Cuff, a New Endotracheal Tube, Effectively Inhibits an Increase in the Cuff Pressure through High Compliance Rather than Low Diffusion of Nitrous Oxide, Anesthesia and Analgesia, Dec. 2001, pp. 140-144, Issue 92.

Sondergaard, Soren. et al., Direct Measurement of Intratracheal Pressure Respitory Monitoring, Pediatric Research, Dec. 2002, vol. 51, No. 3.

Dullenkopf, A. et al., Air Leakage Around Endotracheal Tube Cuffs, European Journal of Anaesthesiology, Dec. 2004, pp. 448-453, Issue 21.

Efrati, Shai MD et al., Optimization of Endotracheal Tube Cuff Filling by Continuous Upper Airway Carbon Dioxide Monitoring, Anesth Analg, 2005, pp. 1081-1088, Issue 101.

Valentino, Joseph MD et al., Utility of Portable Chest Radiographs as a Predictor of Endotracheal Tube Cuff Pressure, Otolaryngology-Head and Neck Surgery, Jan. 1999, pp. 51-56, vol. 1, Issue 120.

Horisberger, T. et al., Measurement of Tracheal Wall Pressure: A Comparison of Three Different in Vitro Techniques, Journal of the Association of Anaesthetists of Great Britain and Ireland, Dec. 2008, pp. 418-422, Issue 63.

Khazin, Vadim MD et al., Gastroesophageal Regurgitation during Anesthesia and Controlled Ventilation with Six Airway Devices, Journal of Clinical Anesthesia, Dec. 2008, pp. 508-513, Issue 20.

Orr, Joseph A., Tracheal Pressure Controller for Ventilators, National Institute of Allergy and Infectious Diseases, Jun. 2010, pp. 1-7.

Gravenstein, D. et al., Breakthroughs in Endotracheal Tube Design and Verification of Tracheal Placement, University of Florida, Office of Technology Licensing, pp. 1-2.

Sheridan ETCO2 Uncuffed Endotracheal Tubes, Monitoring Lumen Tubes, Hudson RCI, 2010, pp. 1-2.

\* cited by examiner

AIRWAY SYSTEM WITH CARBON DIOXIDE SENSOR FOR DETERMINING TRACHEAL CUFF INFLATION AND TECHNIQUE FOR USING THE SAME

RELATED APPLICATION

This application claims priority from U.S. Patent Application No. 61/101,063 which was filed on Sep. 29, 2008, and is incorporated herein by reference in its entirety.

BACKGROUND OF THE INVENTION

1. Field of the Invention

The present invention relates generally to medical devices and, more particularly, to patient ventilation devices, such as breathing circuits and tracheal tubes.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

In the course of treating a patient, a tube or other medical device may be used to control the flow of air, food, fluids, or other substances into the patient. For example, medical devices, such as tracheal tubes, may be used to control the flow of one or more substances into or out of a patient. In many instances it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

For example, tracheal tubes may be used to control the flow of air or other gases through a patient's trachea. Such tracheal tubes may include endotracheal (ET) tubes or tracheostomy tubes. To seal these types of tracheal tubes, an inflatable cuff may be associated with these tubes. When inflated, the cuff generally expands into the surrounding trachea to seal the tracheal passage around the tube. In certain cases, the cuffs may form an imperfect seal against a patient's tracheal wall. For example, there are certain types of low pressure cuffs that are sized to about one and a half times the average tracheal diameter. While these cuffs provide the advantage of low pressure contact with the tracheal walls, when these low pressure cuffs are inflated, the oversize cuffs fold up on themselves to fit in the patient's trachea. The folds serve as leak paths for microbe-laden secretions, which may allow microbes to travel from the patient's mouth into the lungs. Other types of cuffs are manufactured from materials that have a lower tendency to form leak paths. For example, high pressure cuffs are typically made of highly elastic materials that may form a relatively smooth seal against the trachea. However, such cuffs have associated disadvantages. Due to their elastic properties, high pressure cuffs are often inflated to at least twice the intracuff pressure of lower pressure cuffs in order to form a sufficient tracheal seal. Such high pressures may cause patient discomfort. Further, the mechanical pressure of the high pressure cuff against the tracheal walls may also cause temporary damage to cilial structures in the trachea that are associated with airway particle clearance.

SUMMARY

Certain aspects commensurate in scope with the originally claimed invention are set forth below. It should be understood that these aspects are presented merely to provide the reader with a brief summary of certain forms that the invention might take, and that these aspects are not intended to limit the scope of the invention. Indeed, the invention may encompass a variety of aspects that may not be set forth below.

There is provided a system that includes: an endotracheal tube having a proximal end and a distal end adapted for insertion into a patient's airway; an inflatable cuff associated with the distal end of the endotracheal tube; a carbon dioxide sensor adapted to produce an output related to carbon dioxide concentration at a location in the patient's airway proximal to the inflatable cuff; a cuff pressure sensor adapted to produce an output related to an intracuff pressure of the inflatable cuff; and a cuff pressure regulator adapted to change the inflation of the cuff based at least in part on the output from the carbon dioxide sensor and the output from the cuff pressure sensor.

There is also provided a method that includes: receiving an output related to the intracuff pressure of an inflatable cuff associated with an endotracheal tube inserted in a patient's airway; receiving an output related to the carbon dioxide concentration of the patient's airway at a location proximal to the inflatable cuff; and adjusting the inflation of the cuff if the intracuff pressure is below a predetermined pressure threshold and the carbon dioxide concentration in the airway is greater than a predetermined carbon dioxide threshold.

There is also provided a medical device programmed with instructions for: receiving an output related to the intracuff pressure of an inflatable cuff associated with an endotracheal tube inserted in a patient's airway; receiving an output related to the carbon dioxide concentration of the patient's airway at a location proximal to the inflatable cuff; and performing an operation on the output related to the intracuff pressure and on the output related to the carbon dioxide concentration to determine the quality of a cuff seal.

There is also provided an endotracheal tube that includes a conduit having a proximal end and a distal end adapted for insertion into a patient's airway; an inflatable cuff associated with the distal end of the conduit; a lumen disposed on the conduit in fluid communication with a carbon dioxide sensor adapted to produce an output related to carbon dioxide concentration at a location in the patient's airway proximal to the inflatable cuff; and a lumen disposed on the conduit having an opening at a location proximal to the inflatable cuff, wherein the lumen is adapted to suction secretions away from the cuff.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Because patients may be intubated for days or even weeks, even a high quality seal of the cuff against the tracheal walls may degrade as air slowly leaks out of the cuff. Although there exist devices such as manometers that allow a healthcare provider to spot-check the inflation levels of the cuff, such devices may be time-consuming to operate and may not provide immediate feedback. Others have attempted to monitor carbon dioxide levels in a patient's airway above the top of the cuff. When a cuff has a high-quality seal against the trachea, lung exhalations rich in carbon dioxide travel through the endotracheal tube and not the airway, resulting in near-zero carbon dioxide levels in the portion of the airway above the cuff seal. In such a case, it is envisioned that the inflation of the cuff is increased if carbon dioxide levels are high in the airway above the cuff. However, information about carbon dioxide levels in the airway may not be sufficient to determine if a cuff is dislodged. Increasing the inflation volume in that instance may not serve to improve the quality of the seal and may result in damage to the tracheal walls from an overinflated cuff.

It is desirable to provide an airway device including an endotracheal tube or other airway sealing device with an improved tracheal seal. By monitoring the carbon dioxide levels in the patient's airway above the cuff as well as the pressure within the cuff, it is possible to determine the condition of the cuff, i.e., whether the cuff is properly inflated and/or properly placed in the airway. A fully inflated cuff, when properly placed in the patient's airway, will effectively prevent carbon dioxide in the lungs from entering the airway space above the cuff. The respiratory gases will almost exclusively enter and exit the lungs through the conduit in the endotracheal tube. Accordingly, a carbon dioxide sensor placed in the airway space above the cuff should normally indicate relatively low levels of carbon dioxide. When the cuff is underinflated, the tracheal seal may degrade, resulting in the egress of expired carbon dioxide from the lungs into the airway space above the cuff. In such an example, the intracuff pressure may be low thus allowing the carbon dioxide levels in the airway above the cuff to increase. Conversely, when a cuff is overinflated in the airway, the intracuff pressure may be higher than normal while the carbon dioxide levels may be low, indicating an effective seal, but at less desirable higher pressure. When the cuff is dislodged, through patient movement such as coughing, the intracuff pressure may be normal or high, while the carbon dioxide levels in the airway above the cuff may also be high. By combining information about the intracuff pressure with information about the carbon dioxide levels in the airway space above the cuff, a clinician may determine the cuff condition (e.g. if the cuff is properly inflated, overinflated, underinflated, or dislodged within the airway.)

In certain embodiments, the present techniques may be used in conjunction with any appropriate medical device, including a feeding tube, an endotracheal tube, a tracheostomy tube, a circuit, an airway accessory, a connector, an adapter, a filter, a humidifier, a nebulizer, nasal cannula, or a laryngeal mask. The present techniques may also be used to monitor any patient benefiting from mechanical ventilation. Further, the devices and techniques provided herein may be used to monitor a human patient, such as a trauma victim, an intubated patient, a patient with a tracheostomy, an anesthetized patient, a cardiac arrest victim, a patient suffering from airway obstruction, or a patient suffering from respiratory failure.

Figure 1:
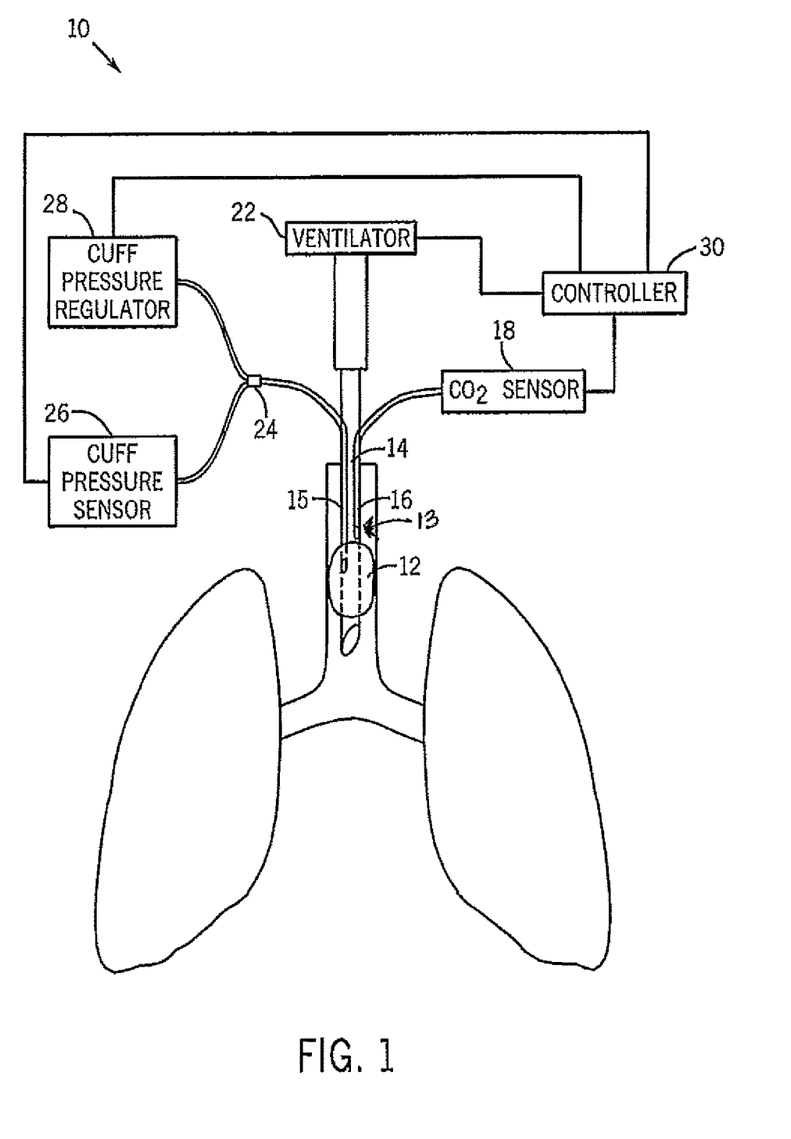
FIG. 1 illustrates an exemplary patient breathing system with a carbon dioxide sensor and cuff pressure sensor in accordance with aspects of the present techniques.

FIG. 1 illustrates a schematic of an exemplary patient breathing system 10. As depicted, the breathing system 10 may include an endotracheal tube 14 with an inflatable cuff 12 that may be inflated to form a seal against the tracheal walls. Typically, the cuff 12 is disposed, adhesively or otherwise, towards the distal end of the endotracheal tube 14. The cuff 12 may be inflated and deflated via an inflation lumen 15 in communication with the cuff 12, typically through a hole or a notch in the tube 14. The cuff 12 may be formed from materials having suitable mechanical properties (such as puncture resistance, pin hole resistance, tensile strength), chemical properties (such as forming a suitable bond to the tube 14), and biocompatibility. In one embodiment, the walls of the inflatable cuff 12 are made of polyurethane having suitable mechanical and chemical properties. An example of a suitable polyurethane is Dow Pellethane® 2363-90A. In another embodiment, the walls of the inflatable cuff 12 are made of a suitable polyvinyl chloride (PVC). Suitable materials may also include polyethylene teraphthalate (PETP), low-density polyethylene (LDPE), polypropylene, silicone, neoprene, or polyisoprene.

The airway space above the cuff 12 (i.e. proximal to the cuff 12) is indicated by reference numeral 13. A carbon dioxide sensor 18 may be associated with the endotracheal tube 14 in order to measure carbon dioxide in the proximal airway space 13. The carbon dioxide sensor 18 may be in fluid communication with the proximal airway space 13. As depicted, a tube 14 may include a lumen 16 that may suction respiratory gases in the proximal airway space 13 for analysis at a carbon dioxide sensor 18 that is proximally located from the endotracheal tube 14. In certain embodiments, an endotracheal tube 14 including a lumen for suctioning secretions off the cuff 12 may be adapted for use with the present techniques. For example, the Hi-Lo™ Evac endotracheal tube, available from Covidien Inc. (Boulder, Colo.), includes a suction lumen that is positioned to suction secretions in the proximal space 13. The suction lumen may be operatively connected to a carbon dioxide sensor 18 in order to deliver respiratory gases to the carbon dioxide sensor 18. In another embodiment, a tube 14 such as the Hi-Lo™ Evac endotracheal tube may be modified to include a separate carbon dioxide sampling lumen 16 in addition to a lumen adapted to suction secretions from the cuff 12. In an alternative embodiment (not shown), the carbon dioxide sensor 18 may be located directly on the endotracheal tube 14. In such an embodiment, the carbon dioxide levels may be measured In suit rather than being measured at a proximal location.

A carbon dioxide sensor 18 as described herein may include any appropriate sensor or sensor element for assessing expired carbon dioxide, including chemical, electrical, optical, non-optical, quantum-restricted, electrochemical, enzymatic, spectrophotometric, fluorescent, or chemiluminescent indicators or transducers. In certain embodiments, the carbon dioxide sensor 18 may include optical components, e.g., an emitter and detector pair that may be of any suitable type. For example, the emitter may be one or more light emitting diodes adapted to transmit one or more wavelengths of light in the red to infrared range, and the detector may be one or more photodetectors selected to receive light in the range or ranges emitted from the emitter. Alternatively, an emitter may also be a laser diode or a vertical cavity surface emitting laser (VCSEL). An emitter and detector may also include optical fiber sensing components. An emitter may include a broadband or "white light" source, in which case the detector could include any of a variety of elements for selecting specific wavelengths, for example, reflective or refractive elements or interferometers. These kinds of emitters and/or detectors would typically be coupled to the rigid or rigidified sensor via fiber optics. Alternatively, a carbon dioxide sensor 18 may sense light detected through the respiratory gas at a different wavelength from the light emitted into the respiratory gas. Such sensors may be adapted to sense fluorescence, phosphorescence, Raman scattering, Rayleigh scattering and multi-photon events or photoacoustic effects. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the ultrasound, radio, microwave, millimeter wave, infrared, visible, ultraviolet, gamma ray or X-ray spectra.

The carbon dioxide sensor 18 may be an electrochemical transducer (such as, without limitation, a Severinghaus transducer), which may be adapted to detect and measure changes in ambient chemical parameters induced by the presence of critical amounts of carbon dioxide. In one embodiment, the carbon dioxide sensor 18 may include a sensor that employs cyclic voltammetry for carbon dioxide detection. Such sensors are available from Giner, Inc., Newton, Mass. For example, the carbon dioxide sensor 18 may be a thick film catalyst sensor utilizing a proton exchange membrane. Such a carbon dioxide sensor 18 may include thick film screen printed electrodes and an electrochemically reversible metal oxide catalysts. Appropriate catalysts include MO, $M_2O_3$, $MO_2$, where M is a metal that is any suitable metal, including platinum, ruthenium, or iridium. Generally, such sensors operate by sensing chemical reactions caused by proton dissociation from water in which carbon dioxide is dissolved. Dissociated water protons may electrochemically reduce a metal oxide layer of the sensor. The electrochemical reduction of the metal oxide will result in generation of an electrical current, which varies in response to the degree of electrochemical reduction.

In another embodiment, the carbon dioxide sensor 18 may include quantum-restricted components, including carbon nanotubes, buckeyballs, or quantum dots. Generally, quantum-restricted components may be coated or otherwise modified with a compound that is sensitive to the respiratory gas of interest. Interaction of the respiratory gas with the compound may affect the electrical, optical, thermal, or physical properties of the quantum-restricted components such that a signal may result. In one such example, carbon nanotubes may be coated with a carbon dioxide-sensitive compound or polymer, such as a polyethyleneimine and starch polymer. Carbon dioxide may combine with primary and tertiary amines in the polyethyleneimine and starch polymer coating to form carbamates. The chemical reaction alters the charge transfer to the carbon nanotubes and results in an electrical signal. Other suitable polymer coatings may be adapted to sense other respiratory gases of interest, such as oxygen or carbon monoxide. In other embodiments, the quantum-restricted component may include a binding molecule, such as a receptor or an enzyme that is specific for the respiratory gas of interest. One such molecule may include carbonic anhydrase. Binding of the respiratory gas to its receptor may affect a downstream response that may result in a change in the electrical properties of a quantum-restricted component.

The carbon dioxide sensor 18 may also include a semi-conductive sensing element, such as a field-effect transistor (FET) or an ion-sensitive field-effect transistor (ISFET). An ISFET may include a silicon dioxide gate for a pH selective membrane, but gates of other material (e.g., silicon nitride, aluminum oxide) could also be used. Such a sensor may be adapted to sense downstream changes in hydrogen ion concentration in response to changes in carbon dioxide or other respiratory gas concentrations. In certain embodiments, the semi-conductive sensing element may be a film.

Alternatively, the carbon dioxide sensor 18 may include an active ingredient of the indicating element, for example the active ingredient involved in providing the required response signal when exposed to a given concentration of carbon dioxide or other constituents. The active ingredient may be any indicator that is sensitive to the presence of carbon dioxide and that is capable of being calibrated to give a response signal corresponding to a given predetermined concentration of carbon dioxide. The signal may be visual, e.g., a change in color, or electrical. Indicators that provide a color change in a presence of carbon dioxide may include chromogenic pH-sensitive indicators and oxidation/reduction indicators. A chromogenic pH-sensitive indicator may provide a color change upon exposure to a given concentration of carbon dioxide or other metabolites in the presence of other ingredients of the element that provide the appropriate chemical conditions to induce the required color change. For such an indicator to be capable of giving a determination of carbon dioxide, it is typically used in combination with a suitable base that provides an alkaline solution. The hydroxyl ions or amine residues present in the alkaline solution react chemically with carbon dioxide to produce a carbonate, bicarbonate and/or carbamate moiety. The resulting reaction depletes the hydroxyl ion or amine at the interface and thus lowers the pH at the surface of the component impregnated with the indicating element. The lowering of the pH causes a color change in the indicator.

Chromogenic pH-sensitive indicators, according to the present techniques, may include metacresol purple, thymol blue, cresol red, phenol red, xylenol blue, a 3:1 mixture of cresol red and thymol blue, bromthymol blue, neutral red, phenolphthalein, rosolic acid, alpha-naphtholphthalein and orange I. Examples of other indicators that may be used include bromeresol purple, bromphenol red, p-nitrophenol, m-nitrophenol, curcumin, quinoline blue, thymolphthalein and mixtures thereof. Suitable bases include sodium carbonate, lithium hydroxide, sodium hydroxide, potassium hydroxide, potassium carbonate, sodium barbitol, tribasic sodium phosphate, dibasic sodium phosphate, potassium acetate, monoethanolamine, diethanolamine and piperidine.

The carbon dioxide sensor 18 may also include an enzyme-based detection system. For example, one such enzyme may be carbonic anhydrase, which is an enzyme that assists interconversion of carbon dioxide and water into carbonic acid, protons, and bicarbonate ions. As described above, this reaction lowers the pH at the surface of the component impregnated with the indicating element. The lowering of the pH may cause a color change in the indicator. Another such enzyme-based detection system is an enzyme linked immunosorbent assay (ELISA). For example, such an assay may be appropriate when assessing tissue proteins. Thus, the indicator element may include a primary antibody specific for the tissue protein of interest, and a labeled secondary binding ligand or antibody, or a secondary binding ligand or antibody in conjunction with a labeled tertiary antibody or third binding ligand. The label may be an enzyme that will generate color development upon incubating with an appropriate chromogenic substrate. Suitable enzymes include urease, glucose oxidase, alkaline phosphatase or hydrogen peroxidase.

A chemical indicator may be used in conjunction with an electrical or electronic device that is adapted to detect and measure changes in the ambient chemical parameters induced by the presence of critical amounts of carbon dioxide. For example, an optical fiber carbon dioxide sensor 18 may be used to convert a change in a chemical indicator to a quantitative measurement of carbon dioxide in the sample. Generally, such sensors operate by directing light of a predetermined wavelength from an external source through the optical fiber to impinge the chemical indicator. The intensity of the emitted fluorescent light returning along the fiber is directly related to the concentration of carbon dioxide in the sample, as a result of the pH-sensitive indicator material present at the fiber tip (i.e., the pH of the indicator solution is directly related to carbon dioxide concentration, as a result of carbonic acid formation). The emitted light is carried by the optical fiber to a device where it is detected and converted electronically to a carbon dioxide concentration value. The carbon dioxide sensor 18 may additionally have a reference dye present in the indicator composition. The intensity of the light emitted from the reference dye may be used to compensate, via ratioing, the signal obtained from the indicator. Other components may be incorporated into the indicator composition including surfactants, antioxidants and ultraviolet stabilizers. The carbon dioxide sensor 18 may be formed from any appropriate substrate. For example, the carbon dioxide sensor 18 may be filter paper, which may be soaked in, dipped in, or otherwise exposed to the appropriate carbon dioxide-sensing compounds. In certain embodiments, the filter paper may be dipped into a solution containing the indicating compounds on only one side. The carbon dioxide sensor 18 may also be polysulfone, polypropylene, or other polymer substrates. The sensor may be a thin film, or a thicker substrate. A thicker substrate may lead to a slower response time, which may be advantageous in situations in which a sensor is monitoring carbon dioxide levels over a longer period of time. Additionally, the sensing component may have pores of a variety of sizes.

A carbon dioxide sensor 18 may also include a borosilicate sensing element such as those discussed in the U.S. patent application Ser. No. 11/526,393, titled "CARBON DIOXIDE DETECTOR HAVING A BOROSILICATE SUBSTRATE" to Rafael Ostrowski and Martin Debreczeny filed on Sep. 25, 2006, which is hereby incorporated by reference in its entirety herein for all purposes.

The breathing system 10 may also include a pressure regulator 28 and a cuff pressure sensor 26. A valve 24 allows gas from the cuff 12 to be sampled by the cuff pressure sensor 26 or gas controlled by the cuff pressure regulator to flow into or out of the cuff 12. For example, the pressure sensor 26 may include pressure manometer that is in fluid communication with the cuff 12. Alternatively, the pressure sensor 26 may include any suitable pressure transducer, for example, a pressure transducer, a piezoresistive pressure sensor, a solid state pressure sensor, or the like. The pressure sensor 26 may, for example, use commercially available pressure sensors from Microswitch, Honeywell or Sensym. The pressure sensor 26 generates an output related to the intracuff pressure of the cuff 12. The output is provided to a controller 30, which performs an operation on the intracuff pressure output in combination with the carbon dioxide level input and determines if air need to be added to the cuff or removed from the cuff. If it is determined that the inflation state of the cuff should be altered, the pressure regulator 28, which is in fluid communication with a cuff inflation lumen 15, is instructed to either pump air into the cuff 12 or removes air from the cuff 12.

The breathing system 10 may also include devices that facilitate positive pressure ventilation of a patient, such as a ventilator 22. The breathing system 10 may also include a respiratory circuit (not shown) connected to the endotracheal tube 14 that allows one-way flow of expired gases away from the patient and one-way flow of inspired gases towards the patient. The respiratory circuit may include standard medical tubing made from suitable materials such as polyurethane, polyvinyl chloride (PVC), polyethylene teraphthalate (PETP), low-density polyethylene (LDPE), polypropylene, silicone, neoprene, or polyisoprene. In certain embodiments, the ventilator 22 is operatively connected to the cuff pressure regulator 28 such that the ventilator 22 provides the source gas for cuff inflation as well as a vent for any gas that is removed from the cuff 22.

It should be appreciated that the carbon dioxide sensor 18, the ventilator 22, the cuff pressure regulator 28, and the cuff pressure sensor 26 may be coupled to a controller 30 with cables (not shown) or may be coupled to a transmission device (not shown) to facilitate wireless transmission between the carbon dioxide sensor and the controller 30. In certain embodiments, the valve 24 may also be linked to the controller 30 such that the controller 30 may instruct the valve to switch between cuff pressure monitoring to adding or removing air from the cuff. Further, the controller 30 may be a stand-alone device or may be coupled to a patient monitor (not shown), which may include any suitable carbon dioxide monitor, such as those available from Nellcor Puritan Bennett LLC. The controller 30 may include a processor for example, a microprocessor. The controller may include a memory such as a floppy disk drive, a CD drive, internal RAM, or a hard drive of the associated processor. Further, the controller 30 may be pail of a housing that includes a display.

Figure 2:
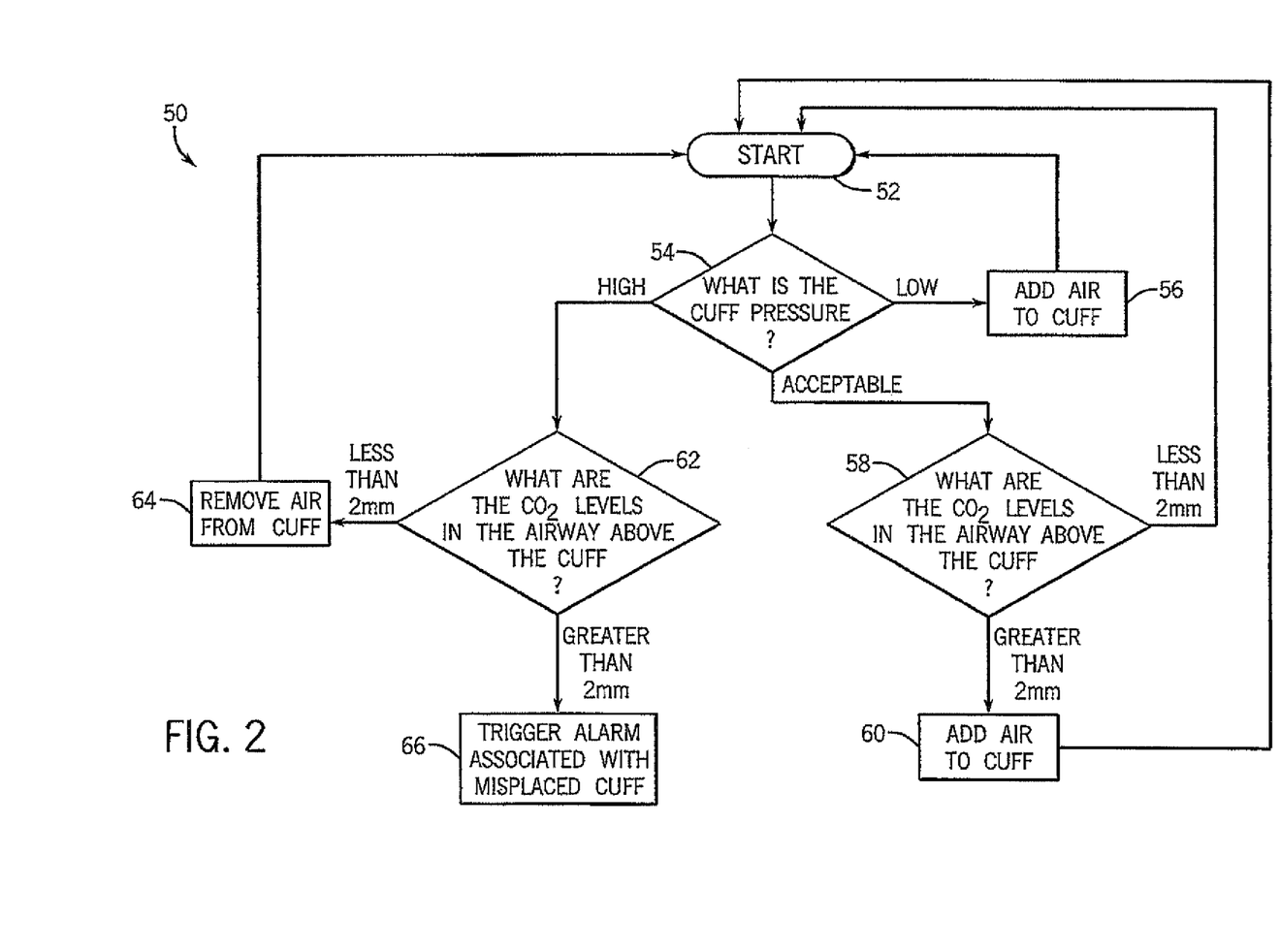
FIG. 2 is a flowchart for monitoring cuff condition in accordance with aspects of the present techniques.

The flow chart 50 depicted in FIG. 2 describes steps involved in monitoring a cuff condition by monitoring intracuff pressure and carbon dioxide levels in the proximal airway space 13. After the start 52, intracuff pressure data is acquired from the cuff pressure sensor 26 and evaluated at step 54. The intracuff pressure may be compared against a minimum value to determine if the intracuff pressure is too low (i.e. the cuff 12 is underinflated) or against a maximum value determine if the intracuff pressure is too high (i.e. the cuff 12 is overinflated). If the intracuff pressure is within an acceptable range, the process moves to step 58, which involves evaluation of carbon dioxide levels in the proximal airway space 13. If the carbon dioxide levels are above a certain threshold, depicted here as above a partial pressure of 2 mm Hg, the controller 30 instructs the cuff pressure regulator 28 to add air to the cuff. If the carbon dioxide levels are below a certain threshold, then the process returns to start 52. If the cuff pressure is low at step 54, air is added to the cuff at step 56 (or 60). If the cuff pressure is high at step 54, the process moves on to step 62 to determine the carbon dioxide levels in the airway. If both the cuff inflation and carbon dioxide levels are high, an alarm associated with a cuff that is misplaced within the airway is triggered at step 66. If the cuff inflation is high, but the carbon dioxide levels are lower than the predetermined threshold, then air is removed from the cuff at step 64. It is envisioned that the process 50 may be repeated at certain timed intervals or may be repeated continuously to monitor the cuff condition. Further, it is envisioned that a controller 30 may include a counter for determining how many times certain steps have been repeated. For example, if step 56, in which air is added to an underinflated cuff, is repeated more than a certain number of times in a predetermined time period, an alarm associated with low cuff pressure may be triggered. Similarly, if step 60, in which air is added to a cuff because carbon dioxide levels in the proximal airway space 13 are low, is repeated more than a certain number of times in a predetermined time period, an alarm or message may be triggered indicating that the cuff pressure should be checked for overinflation.

In specific embodiments, endotracheal cuffs utilizing inflation pressures significantly greater than 25 cm $H_2O$, such as 100 cm $H_2O$, may be referred to as high-pressure cuffs, while cuffs that are designed to be inflated at pressures less than 25 cm $H_2O$ may be considered low-pressure cuffs. It is envisioned that the endotracheal tube 14 may have an information element (not shown) that provides information to the controller 30 about the type of cuff 21 being used by the endotracheal tube 14. The information element may be a coded resistor or EPROM with stored calibration and identification information about the endotracheal tube 14 and cuff 12. Such information may include alarm parameters.

In certain embodiments, an alarm corresponding with underinflation of the cuff 12 may be triggered if the intracuff pressure of a low-pressure cuff is less than 20 cm $H_2O$ or less than 18 cm $H_2O$ and the measured carbon dioxide partial pressure in the proximal airway space 13 is greater than 2 mm Hg or greater than 5 mm Hg. An alarm corresponding with overinflation of the cuff 12 may be triggered if the intracuff pressure of a low pressure cuff is greater than 25 cm $H_2O$ and the measured carbon dioxide partial pressure in the proximal airway space is less than 2 mm Hg or less than 5 mm Hg. Such alarms may be communicated by the controller 30 or by a patient monitor that includes a display. An alarm may be an audio alarm or a visual alarm.

In one particular embodiment, alarm parameters may be customized for patients with certain types of diseases. Generally, healthcare providers seek to normalize intracuff pressure to respiratory circuit pressure, which includes the lungs. If the lung pressure is about equal to the cuff pressure against the tracheal walls, air from the lungs tends not to push against the cuff walls and leak into the proximal airway space 13. In patients with chronic obstructive pulmonary disease, gas pressure inside the respiratory circuit is often higher than normal to overcome greater resistance in the airway. Because lung pressure in these patients may be 40 cm $H_2O$ or greater as opposed to 25 cm $H_2O$, which is a more typical respiratory circuit pressure, an imbalance between intracuff pressure and lung pressure is created. As a result, air tends to leak out of the higher pressure area of the lungs into the proximal airway space 13. In such patients, an alarm for overinflation of the cuff 12 may be triggered if the intracuff pressure of a high-pressure cuff is greater than 30 cm $H_2O$ or 40 cm $H_2O$. Because these patients may have sensitive airway tissue that is particularly susceptible to damage, it may also be beneficial to monitor the carbon dioxide in the proximal airway space 13 for low carbon dioxide levels associated with the lowest possible inflation pressure of the cuff 12.

In certain embodiments, it may be advantageous to employ the techniques provided herein in combination with capnography, which may provide information about carbon dioxide production, pulmonary perfusion, alveolar ventilation, respiratory patterns and elimination of carbon dioxide from the anaesthesia circuit and ventilator. Typically, capnography involves measuring expiratory gas carbon dioxide concentration in the airflow against time during multiple respiratory cycles. As opposed to measuring carbon dioxide levels in the unsealed portion of the airway to determine if the cuff 12 has a good seal against the tracheal walls, in capnography, carbon dioxide levels within the respiratory circuit are assessed. Typically, carbon dioxide levels within a respiratory circuit may be measured with any suitable carbon dioxide sensor. The respiratory circuit carbon dioxide levels measured by the present techniques may produce a graphical capnogram that may illustrate three phases in breath carbon dioxide gas concentration during the patient exhale cycle in a healthy patient. The first phase indicates clearing of the conducting airways which do not normally participate in gas exchange and which are referred to as "dead space." The second phase typically involves exhalation of air from conducting airways dynamically mixed with lung gases from the active (alveoli) membrane surfaces within the lung that have undergone gas exchange with arterial blood. The third phase reflects the exhalation of unmixed gas from regions of the lung that are normally in active exchange with the alveoli tissue. It may be advantageous to synchronize sampling of carbon dioxide levels in the proximal airway space 13 with the second or the third phase of the breathing cycle. In such an embodiment, capnographic data may be processed by controller 30 and synchronized with measurements from the carbon dioxide sensor 18. For example, if higher partial pressure of carbon dioxide in the proximal airway space 13 is detected at points in the breathing cycle associated with expiration, this may be indicative of a pinpoint leak. However, if the partial pressure of carbon dioxide exceeds a predetermined threshold at all points in the breathing cycle, this may be indicative of a larger leak or of a cuff displacement.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of carbon dioxide, but these techniques may also be utilized for the measurement and/or analysis of other respiratory gases. For example, these techniques may be used to monitor oxygen, carbon monoxide, volatile organic compounds such as ethanol, metabolic trace gases such as acetone, or anesthetic gases such as isoflurane, halothane, desflurane, sevoflurane, and enflurane. Additionally, respiratory gases associated with an acute or chronic disease state may be monitored using the present techniques. Rather, the invention is to cover all modifications, equivalents, and alternatives falling within the spirit and scope of the invention as defined by the following appended claims. It will be appreciated by those working in the art that sensors fabricated using the presently disclosed and claimed techniques may be used in a wide variety of contexts. That is, while the invention has primarily been described in conjunction with the measurement of carbon dioxide concentration in the airway, the airways products fabricated using the present method may be used to evaluate any number of sample types in a variety of industries, including fermentation technology, cell culture, and other biotechnology applications.

The invention claimed is:

1. A system comprising:
    an endotracheal tube having a proximal end and a distal end configured to inserted into a patient's airway;
    an inflatable cuff disposed about the distal end of the endotracheal tube, wherein the inflatable cuff is configured to form a seal with a wall of the patient's airway;
    a carbon dioxide sensor configured to produce an output related to carbon dioxide concentration at a location in the patient's airway proximal to the inflatable cuff;
    a cuff pressure sensor configured to produce an output, wherein the output comprises a direct measurement of an intracuff pressure of the inflatable cuff;
    a cuff pressure regulator configured to change the inflation of the cuff based at least in part on the output from the carbon dioxide sensor and the output from the cuff pressure sensor;
    a controller operatively coupled to the cuff pressure regulator and configured to determine whether the inflatable cuff is properly inflated and whether the inflatable cuff properly placed in the patient's airway based at least in part upon the output from the carbon dioxide sensor and the output from the cuff pressure sensor, wherein the controller is configured to:
        cause the cuff pressure regulator to add air to the inflatable cuff in response to a determination that the intracuff pressure is less than a predetermined low pressure threshold;
        cause the cuff pressure regulator to add air to the inflatable cuff in response to a determination that the intracuff pressure does not violate a threshold and the carbon dioxide concentration is greater than a predetermined carbon dioxide threshold;
        cause the cuff pressure regulator to remove air from the inflatable cuff in response to a determination that the intarcuff pressure is greater than a predetermined high pressure threshold and the carbon dioxide concentration is less than the predetermined carbon dioxide threshold; and
        trigger an alarm that is triggered if in response to a determination that the inflatable cuff is misplaced in the patient's airway, wherein the controller is configured to determine that the inflatable cuff is misplaced in response to a determination that the intracuff pressure is above the predetermined high pressure threshold and the carbon dioxide concentration in the airway is greater than the predetermined carbon dioxide threshold; and
    an information element disposed on the endotracheal tube, wherein the information element comprises stored data related to the inflatable cuff, the predetermined high pressure threshold, and the predetermined carbon dioxide threshold.

2. The system of claim 1, wherein the predetermined carbon dioxide threshold is about 2 mm Hg and the predetermined low pressure threshold is about 20 cm H₂O.

3. The system of claim 1, wherein the controller is configured to trigger comprising an alarm that is triggered if the intracuff pressure is below the predetermined low pressure threshold and the carbon dioxide concentration in the airway is greater than the predetermined carbon dioxide threshold.

4. The system of claim 1, wherein the predetermined carbon dioxide threshold is about 2 mm Hg and the predetermined high pressure threshold is about 25 cm H₂O.

5. The system of claim 1, comprising a ventilator to which the endotracheal tube is operatively connected.

6. The system of claim 5, wherein the ventilator is operatively connected to an inflation line of the cuff to allow the cuff to be inflated.

7. The system of claim 1, wherein the carbon dioxide sensor comprises a chemical indicator, an electrochemical transducer, a non-optical transducer, an optical transducer, or a quantum-restricted element.

8. The system of claim 1, wherein the carbon dioxide sensor is disposed on the endotracheal tube.

9. The system of claim 1, wherein the endotracheal tube comprises a suction lumen adapted to delivery airway gases to a distally located carbon dioxide sensor.

10. The system of claim 1, wherein the cuff pressure sensor comprises a manometer.

11. A method comprising the steps of:
    receiving a direct measurement of the intracuff pressure of an inflatable cuff disposed about a distal end of an endotracheal tube inserted in a patient's airway, wherein the inflatable cuff is configured to form a seal with a wall of the patient's airway;
    receiving an output related to a carbon dioxide concentration of the patient's airway at a location proximal to the inflatable cuff;
    receiving information relating to a predetermined high pressure threshold and a predetermined carbon dioxide threshold from an information element disposed on the endotracheal tube;
    determining that the inflatable cuff is misplaced in the patient's airway in response to a determination that the intracuff pressure is above the predetermined high pressure threshold and the carbon dioxide concentration in the airway is greater than the predetermined carbon dioxide threshold; and
    triggering an alarm in response to the determination that the inflatable cuff is misplaced if the intracuff pressure is above the predetermined high pressure threshold and the carbon dioxide concentration in the airway is greater than the predetermined carbon dioxide threshold.

12. The method of claim 11, comprising providing instructions to add more air to the cuff if the intracuff pressure falls below a predetermined low pressure threshold and the carbon dioxide concentration in the airway is greater than the predetermined carbon dioxide threshold.

13. The method of claim 11, comprising providing instructions to remove air from the cuff if the intracuff pressure is above a predetermined high pressure threshold and the carbon dioxide concentration in the airway is greater than the predetermined carbon dioxide threshold.

14. The method of claim 11, wherein the predetermined high pressure threshold is about 25 cm H₂O.

15. A medical device programmed with instructions for:
    receiving a direct measurement of the intracuff pressure of an inflatable cuff disposed about a distal end of an endotracheal tube inserted in the patient's airway, wherein the inflatable cuff is configured to form a seal with the wall of the patient's airway;
    receiving an output related to the carbon dioxide concentration of the patient's airway at a location proximal to the inflatable cuff;
    receiving information relating to a predetermined high pressure threshold and a predetermined carbon dioxide threshold from an information element disposed on the endotracheal tube;
    providing instructions for adding more air to the inflatable cuff in response to a determination that the intracuff pressure is less than a predetermined low pressure threshold and the carbon dioxide concentration in the airway is greater than the predetermined carbon dioxide threshold;

providing instructions for adding more air to the inflatable cuff in response to a determination that the intracuff pressure is less than the predetermined high pressure threshold and the carbon dioxide concentration in the airway is greater than the predetermined carbon dioxide threshold;

providing instructions to remove air from the inflatable cuff in response to a determination that the intracuff pressure is greater than the predetermined high pressure threshold and the carbon dioxide concentration in the airway is less than the predetermined carbon dioxide threshold; and triggering an alarm in response to a determination that the inflatable cuff is misplaced in the patient's airway, wherein determining that the inflatable cuff is misplaced in the airway comprises determining that the intracuff pressure is above the predetermined high pressure threshold and the carbon dioxide concentration in the airway is greater than the predetermined carbon dioxide threshold.

16. The device of claim 15, comprising receiving an input related to the patient's clinical condition, wherein the patient's clinical condition is used to select the predetermined high pressure threshold.

17. The device of claim 16, wherein the predetermined high pressure threshold is about 30 cm $H_2O$ when the patient's clinical condition is chronic obstructive pulmonary disease.

* * * * *